United States Patent
Tai et al.

(10) Patent No.: US 9,029,158 B2
(45) Date of Patent: May 12, 2015

(54) MICROFLUIDIC DEVICE

(71) Applicant: California Institute of Technology, Pasadena, CA (US)

(72) Inventors: Yu-Chong Tai, Pasadena, CA (US); Siyang Zheng, Pasadena, CA (US); Jeffrey Chun-Hui Lin, Pasadena, CA (US); Harvey Kasdan, Chatsworth, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/296,199

(22) Filed: Jun. 4, 2014

(65) Prior Publication Data

US 2014/0377742 A1 Dec. 25, 2014

Related U.S. Application Data

(62) Division of application No. 12/062,808, filed on Apr. 4, 2008, now abandoned.

(60) Provisional application No. 60/922,296, filed on Apr. 6, 2007.

(51) Int. Cl.
*G01N 15/06* (2006.01)
*G01N 33/50* (2006.01)
(Continued)

(52) U.S. Cl.
CPC ....... *G01N 33/5094* (2013.01); *B01L 3/502753* (2013.01); *B01L 3/502761* (2013.01); *B01L 2200/0636* (2013.01); *B01L 2200/0647* (2013.01); *B01L 2300/0681* (2013.01); *B01L 2300/0816* (2013.01);
(Continued)

(58) Field of Classification Search
USPC ............ 422/50, 58, 68.1, 100, 102, 502, 503; 436/174, 180, 43, 56
See application file for complete search history.

(56) References Cited

U.S. PATENT DOCUMENTS 4,233,029 A 11/1980 Columbus
4,376,820 A 3/1983 Giannini et al.
(Continued)

FOREIGN PATENT DOCUMENTS

WO WO 01/68238 A2 9/2001
WO WO 2006/055816 5/2006
(Continued)

OTHER PUBLICATIONS

Groselj-Gren, et al. Neutrophil and monocyte CD64 and CD163 expression in critically ill neonates and children with sepsis: comparison of fluorescence intensities and calculated indexes. Mediators Inflamm. (2008), vol. 2008, p. 1-10; article ID 202646; doi: 10.1155/2008/202646.
(Continued)

*Primary Examiner* — Brian J Sines
(74) *Attorney, Agent, or Firm* — Hema Vakharia-Rao; Nixon Peabody LLP (57) ABSTRACT

Described herein are particular embodiments relating to a microfluidic device that may be utilized for cell sensing, counting, and/or sorting. Particular aspects relate to a microfabricated device that is capable of differentiating single cell types from dense cell populations. One particular embodiment relates a device and methods of using the same for sensing, counting, and/or sorting leukocytes from whole, undiluted blood samples.

19 Claims, 10 Drawing Sheets

(51) Int. Cl.
*G01N 33/58* (2006.01)
*B01L 3/00* (2006.01)
*G01N 15/10* (2006.01)
*G01N 15/14* (2006.01)

(52) U.S. Cl.
CPC . *B01L 2300/0822* (2013.01); *B01L 2300/0864* (2013.01); *B01L 2300/0877* (2013.01); *B01L 2400/086* (2013.01); *G01N 15/1056* (2013.01); *G01N 15/1484* (2013.01); *G01N 2015/1006* (2013.01); *G01N 2015/1486* (2013.01); *G01N 2015/149* (2013.01); *G01N 33/582* (2013.01)

(56) References Cited

U.S. PATENT DOCUMENTS

| | | | |
|---|---|---|---|
| 4,400,370 | A | 8/1983 | Kass |
| 4,882,284 | A | 11/1989 | Kirchanski et al. |
| 5,304,487 | A | 4/1994 | Wilding et al. |
| 5,716,852 | A | 2/1998 | Yager et al. |
| 5,837,115 | A | 11/1998 | Austin et al. |
| 5,932,100 | A | 8/1999 | Yager et al. |
| 5,972,710 | A | 10/1999 | Weigl et al. |
| 6,136,610 | A | 10/2000 | Polito et al. |
| 6,372,516 | B1 | 4/2002 | Sun |
| 6,426,230 | B1 | 7/2002 | Feistel |
| 6,551,841 | B1 | 4/2003 | Wilding et al. |
| 6,635,163 | B1 | 10/2003 | Han et al. |
| 6,637,463 | B1 | 10/2003 | Lei et al. |
| 6,674,525 | B2 | 1/2004 | Bardell et al. |
| 6,852,284 | B1 | 2/2005 | Holl et al. |
| 7,105,355 | B2 | 9/2006 | Kurabayashi et al. |
| 7,192,560 | B2 | 3/2007 | Parthasarathy et al. |
| 7,247,274 | B1 | 7/2007 | Chow |
| 7,347,976 | B2 | 3/2008 | Parthasarathy et al. |
| 7,553,453 | B2 | 6/2009 | Gu et al. |
| 7,718,421 | B2 | 5/2010 | Chen et al. |
| D669,191 | S | 10/2012 | Handique |
| 8,318,109 | B2 | 11/2012 | Saltsman et al. |
| 8,364,418 | B2 | 1/2013 | Davis et al. |
| 8,518,705 | B2 | 8/2013 | Chan et al. |
| 2001/0008760 | A1 | 7/2001 | King et al. |
| 2002/0031255 | A1 | 3/2002 | Kasdan et al. |
| 2003/0002037 | A1 | 1/2003 | Kasdan et al. |
| 2003/0073089 | A1 | 4/2003 | Mauze et al. |
| 2003/0170881 | A1 | 9/2003 | Davis et al. |
| 2004/0126008 | A1 | 7/2004 | Chapoulaud et al. |
| 2005/0105077 | A1 | 5/2005 | Padmanabhan et al. |
| 2006/0011862 | A1 | 1/2006 | Bernstein |
| 2007/0227890 | A1 | 10/2007 | Ramsey et al. |
| 2007/0253868 | A1 | 11/2007 | Beebe et al. |
| 2007/0292941 | A1 | 12/2007 | Handique et al. |
| 2008/0101993 | A1 | 5/2008 | Andersson et al. |
| 2008/0212102 | A1 | 9/2008 | Nuzzo et al. |
| 2009/0042241 | A1 | 2/2009 | Yu-Chong et al. |
| 2009/0117605 | A1 | 5/2009 | Davis et al. |
| 2010/0051124 | A1 | 3/2010 | Imran |
| 2010/0093019 | A1 | 4/2010 | Ditcham et al. |
| 2011/0184537 | A1 | 7/2011 | Kasdan et al. |
| 2012/0071342 | A1 | 3/2012 | Lochhead et al. |
| 2012/0266986 | A1 | 10/2012 | Wimberger-Friedl et al. |
| 2012/0275972 | A1 | 11/2012 | Schoen et al. |
| 2013/0137135 | A1 | 5/2013 | Tai et al. |
| 2013/0230867 | A1 | 9/2013 | Davis et al. |

FOREIGN PATENT DOCUMENTS

| | | |
|---|---|---|
| WO | WO 2006/118586 A2 | 11/2006 |
| WO | WO 2008/121828 | 10/2008 |
| WO | WO 2008/124589 A2 | 10/2008 |
| WO | WO 2009/144660 | 12/2009 |
| WO | WO 2011/094577 A2 | 8/2011 |
| WO | WO 2011/128893 A3 | 10/2011 |
| WO | WO 2012/092010 | 7/2012 |
| WO | WO 2014/097286 | 6/2014 |
| WO | WO 2014/097287 | 6/2014 |

OTHER PUBLICATIONS

Notice of Allowance dated Aug. 21, 2014 for U.S. Appl. No. 14/296,317.
U.S. Appl. No. 60/922,296, filed Apr. 6, 2007, Tai et al.
Adams, et al. Fluorometric characterization of six classes of human leukocytes. Acta Cytol. Sep.-Oct. 1974; 18(5): 389-391.
Adams, et al. Machine characterization of human leukocytes by acridine orange fluorescence. Acta Cytol. May-Jun. 1971; 15(3): 289-291.
Altendorf, et al. Differential Blood Cell Counts Obtained Using a Microchannel Based Flow Cytometer. Transducers. Jun. 1997 16-19; 1: 531-534.
Assicot, et al. High serum procalcitonin concentrations in patients with sepsis and infection. Lancet. Feb. 27, 1993; 341(8844): 515-518.
Aulesa, et al. Validation of the Coulter LH 750 in a hospital reference laboratory. Lab Hematol. 2003; 9(1): 15-28.
Ault, Kenneth A. Flow cytometric measurement of platelet function and reticulated platelets. Annals of the New York Academy of Sciences. Mar. 20, 1993; 677: 293-308.
Bhattacharya, et al. Studies on Surface Wettability of Poly(Dimethyl) Siloxane (PDMS) and Glass Under Oxygen-Plasma Treatment and Correlation With Bond Strength. J. Microelectromechan. Syst. Jun. 2005; 14: 590-597.
Blajchman, et al. Bacterial detection of platelets: current problems and possible resolutions. Transfusion medicine reviews. Oct. 2005;19(4):259-272.
Bodensteiner, David C. A flow cytometric technique to accurately measure post-filtration white blood cell counts. Transfusion. Sep. 1989; 29(7): 651-653.
Cheson, et al. National Cancer Institute-sponsored Working Group guidelines for chronic lymphocytic leukemia: revised guidelines for diagnosis and treatment. Blood. 1996; 87(12): 4990-4997.
Christ-Crain, et al. Effect of procalcitonin-guided treatment on antibiotic use and outcome in lower respiratory tract infections: cluster-randomised, single-blinded intervention trial. Lancet. Feb. 21, 2004; 363(9409): 600-607.
Cristofanilli, et al. Circulating tumor cells, disease progression, and survival in metastatic breast cancer. N Engl J Med. Aug. 19, 2004; 351(8): 781-791.
Davis, et al. Neutrophil CD64 is an improved indicator of infection or sepsis in emergency department patients. Arch Pathol Lab Med. May 2006; 130(5): 654-661.
Dieye, et al. Absolute CD4 T-cell counting in resource-poor settings: direct volumetric measurements versus bead-based clinical flow cytometry instruments. J Acquir Immune Defic Syndr. May 1, 2005; 39(1): 32-37.
Divers, et al. Quantitation of CD62, soluble CD62, and lysosome-associated membrane proteins 1 and 2 for evaluation of the quality of stored platelet concentrates. Transfusion. Apr. 1995; 35(4): 292-297.
Drexler, et al. Diagnostic value of immunological leukemia phenotyping. Acta Haematol. 1986; 76(1): 1-8.
Dziegiel, et al. Detecting fetomaternal hemorrhage by flow cytometry. Curr Opin Hematol. Nov. 2006; 13(6): 490-495.
Fischer, et al. Reducing costs in flow cytometric counting of residual white blood cells in blood products: utilization of a single platform bead free flow rate calibration method. Transfusion. Jul. 2011; 51(7): 1431-1438.
Fujimoto, Keiji. Principles of Measurement in Hematology Analyzers Manufactured by Sysmex Corporation. Sysmex Journal International. 1999; 9(1): 31-44.
Gawad, et al. Micromachined impedance spectroscopy flow cytometer for cell analysis and particle sizing. Lab Chip. Sep. 2001; 1(1): 76-82.
Graff, et al. Close relationship between the platelet activation marker CD62 and the granular release of platelet-derived growth factor. J Pharmacol Exp Ther. Mar. 2002; 300(3): 952-957.

(56) References Cited

OTHER PUBLICATIONS

Guerti, et al. Performance evaluation of the PENTRA 60C+ automated hematology analyzer and comparison with the ADVIA 2120. Int J Lab Hematol. Apr. 2009; 31(2): 132-141.

Hawkins, Robert C. Laboratory turnaround time. The Clinical Biochemist Reviews. Nov. 2007; 28(4): 179-194.

Hershman, et al. Monocyte HLA-DR antigen expression characterizes clinical outcome in the trauma patient. Br. J. Surg. Feb. 1990; 77(2): 204-207.

Hilfrich, et al. Prognostic relevance of human papillomavirus L1 capsid protein detection within mild and moderate dysplastic lesions of the cervix uteri in combination with p16 biomarker. Anal Quant Cytol Histol. Apr. 2008; 30(2): 78-82.

Hillier, et al. A case-control study of chorioamnionic infection and histologic chorioamnionitis in prematurity. N. Engl. J. Med. Oct. 13, 1988; 319(15): 972-978.

Hoffmann, Johannes JML. Neutrophil CD64 as a sepsis biomarker. Biochem Med (Zagreb). 2011; 21(3): 282-290.

Holmes, et al. High throughput particle analysis: combining dielectrophoretic particle focussing with confocal optical detection. Biosens Bioelectron. Feb. 15, 2006; 21(8): 1621-1630.

Hughes-Jones, et al. Differential white cell counts by frequency distribution analysis of cell volumes. J. Clin. Pathol. Aug. 1974; 27(8): 623-625.

IPRP and WO in PCT/US2008/059408, dated Oct. 6, 2009.

Jackson, JF. Supravital blood studies, using acridine orange fluorescence. Blood. May 1961; 17: 643-649.

Kass, L. Identification of lymphocyte subpopulations with a polymethine dye. J. Histochem. Cytochem. Jul. 1988; 36(7): 711-715.

Kass, L. Staining of granulocytic cells by Chlorazol black E. Am J. Clin. Pathol. Dec. 1981; 76(6): 810-812.

Kibe, et al. Diagnostic and prognostic biomarkers of sepsis in critical care. J Antimicrob Chemother. Apr. 2011; 66 Suppl 2: ii33-40.

Larosa, et al. Biomarkers: the future. Crit. Care Clin. Apr. 2011; 27(2): 407-419.

Lee, et al. A flow-rate independent counter using a fixed control volume between double electrical sensing zones. Proceedings of the 18th IEEE International Conference on Micro Electro Mechanical Systems (MEMS). 2005. 678-681.

Lee, et al. Micromachine-based multi-channel flow cytometers for cell/particle counting and sorting. J. Micromechanics and Microengineering. 2005; 15(3): 447-454.

Liu, et al. Improved quantitative Apt test for detecting fetal hemoglobin in bloody stools of newborns. Clin. Chem. Nov. 1993; 39(11 Pt 1): 2326-2329.

Lotan, et al. Bladder cancer screening in a high risk asymptomatic population using a point of care urine based protein tumor marker. J Urol. Jul. 2009; 182(1): 52-57.

Masse, et al. Validation of a simple method to count very low white cell concentrations in filtered red cells or platelets. Transfusion. Jul.-Aug. 1992; 32(6): 565-571.

Matic, et al. Whole blood analysis of reticulated platelets: improvements of detection and assay stability. Cytometry. Oct. 15, 1998; 34(5): 229-234.

McDonald, et al. Use of a solid-phase fluorescent cytometric technique for the detection of bacteria in platelet concentrates. Transfus Med. Jun. 2005; 15(3): 175-183.

Michelson, Alan D. Flow cytometry: a clinical test of platelet function. Blood. Jun. 15, 1996; 87(12): 4925-4936.

Miller, et al. Proteomics in Microfluidic Devices. In Encyclopedia of Micro- and Nanofluidics; Li, D. Q., Ed.; Springer: Heidelberg, Germany, 2008; 3: 1749-1758.

Morgan, et al. High speed simultaneous single particle impedance and fluorescence analysis on a chip. Curr. Appl. Phys. 2006; 6: 367-370.

Moriyama, et al. Acridine Orange as a Fluorescent Probe for Lysosomal Proton Pump3. J. Biochem. 1982; 92: 1333-1336.

Moro, et al. A new broad-spectrum cancer marker. Vitro Diagnostic Technology. Jun. 1, 2005; 1-3.

Niehren, et al. An All-Solid-State Flow Cytometer for Counting Fluorescent Microspheres. Anal. Chem. 1995; 67(15): 2666-2671.

OA in CN 200880015296.7, dated Sep. 20, 2012.

Oberjat, et al. Rapid and reliable differential counts on dilute leukocyte suspensions. J. Lab. Clin. Med. Sep. 1970; 76(3): 518-522.

Perry, et al. Is low monocyte HLA-DR expression helpful to predict outcome in severe sepsis? Intensive Care Med. Aug. 2003;29(8):1245-1252.

Ramakumar, et al. Comparison of screening methods in the detection of bladder cancer. J Urol. Feb. 1999; 161(2): 388-394.

Rawstron, et al. Quantitation of minimal disease levels in chronic lymphocytic leukemia using a sensitive flow cytometric assay improves the prediction of outcome and can be used to optimize therapy. Blood. Jul. 1, 2001; 98(1): 29-35.

Rodriguez, et al. A microchip CD4 counting method for HIV monitoring in resource-poor settings. PLoS Med. Jul. 2005; 2(7): e182.

Rylatt, et al. An immunoassay for human D dimer using monoclonal antibodies. Thromb Res. Sep. 15, 1983; 31(6): 767-778.

Sacks, et al. Guidelines and recommendations for laboratory analysis in the diagnosis and management of diabetes mellitus. Clin Chem. Mar. 2002; 48(3): 436-472.

Satake, et al. A sensor for blood cell counter using MEMS technology. Sensors and Actuators B: Chemical. 2002; 83(1): 77-81.

Segal, et al. Accuracy of platelet counting haematology analysers in severe thrombocytopenia and potential impact on platelet transfusion. Br. J. Haematol. Feb. 2005; 128(4): 520-525.

Shapiro, et al. Combined blood cell counting and classification with fluorochrome stains and flow instrumentation. J Histochem Cytochem. Jan. 1976; 24(1): 396-411.

Shapiro, et al. Cytomat-R: a computer-controlled multiple laser source multiparameter flow cytophotometer system. J Histochem Cytochem. Jul. 1977; 25(7): 836-844.

Sheehan, et al. An improved method of staining leucocyte granules with Sudan black B. J Pathol Bacteriol. Jan.-Apr. 1947; 59(1-2): 336-337.

Simonnet, et al. High-throughput and high-resolution flow cytometry in molded microfluidic devices. Anal Chem. Aug. 15, 2006; 78(16): 5653-5663.

Stein, et al. D-dimer for the exclusion of acute venous thrombosis and pulmonary embolism: a systematic review. Ann Intern Med. Apr. 20, 2004; 140(8): 589-602.

Steinkamp, et al. Multiparameter Cell Sorting: Identification of Human Leukocytes by Acridine Orange Fluorescence. Acta Cytol. 1973; 17: 113-117.

Sutherland, et al. The ISHAGE guidelines for CD34+ cell determinaton by flow cytometry. J Hematother. Jun. 1996; 5(3): 213-226.

Tatsumi, et al. Principle of blood cell counter—development of electric impedance method. Sysmex J. Int. 1999; 9(1): 8-20.

Tibbe, et al. Optical tracking and detection of immunomagnetically selected and aligned cells. Nat Biotechnol. Dec. 1999; 17(12): 1210-1213.

Van Dilla, et al. Volume distribution and separation of normal human leucocytes. Proc. Soc. Exp. Bio. Med. Jun. 1967; 125(2):367-370.

Wang, et al. "Reticulated platelets predict platelet count recovery following chemotherapy." Transfusion. Mar. 2002; 42(3): 368-374.

Weigl, et al. Design and rapid prototyping of thin-flim laminate-based microfluidic devices. Biomed Microdev. 2001; 3: 267-274.

Yang, et al. A cell counting/sorting system incorporated with a microfabricated flow cytometer chip. Meas. Sci. Technol. 2006; 17: 2001-2009.

MICROFLUIDIC DEVICE

CROSS-REFERENCE TO RELATED APPLICATIONS

This present application is a divisional of U.S. Ser. No. 12/062,808, filed Apr. 4, 2008, currently pending, which claims the benefit of priority of U.S. provisional application No. 60/922,296, filed Apr. 6, 2007, the contents of each which are herein incorporated by reference in their entirety.

STATEMENT OF GOVERNMENT INTEREST

This work was supported in part by the National Space Biomedical Research Institute through NASA, grant number NCC 9-58-317. The United States government has certain rights in this invention.

FIELD OF THE INVENTION

The present disclosure relates to fabricated microfluidic devices that can be utilized as cell sensors and/or actuators. In certain embodiments, the microfluidic device may be used for labeling, sensing differentiating, and/or sorting targets, particularly cell populations.

BACKGROUND OF THE INVENTION

Standard cell sensors or actuators are generally based on flow cytometry and employ one or a combination of electrical impedance sensing, light scattering measurement, and chemical or immunostaining followed by optical sensing.

For differentiation of blood cells by electrical impedance sensing, red blood cells are removed by lysing in order to reduce the blood volume. Lysing is generally done through the use of saponin or surfactants. During the lysing process, the leukocyte cell volume changes depending on cell type, due to the leakage of cytoplasm contents and cell nucleus shrinkage in varying amounts. Fujimoto, *Sysmex J. Int.* 9 (1999). Thus, normally 2-part (lymphocytes versus granulocytes) or even 3-part (lymphocytes, neutrophils, and other leukocytes) differential can be achieved by simple electrical impedance measurement of particle volume. Hughes-Jones, et al., *J. Clin. Patol.* 27; 623-625 (1974); Oberjat, et al., *J. Lab. Clin. Med.* 76; 518 (1970); Vandilla, et al., *Proc. Soc. Exp. Biol. Med.* 125; 367 (1967); Maeda, et al., *Clin. Pathol.* 27; 1117-1200 (1979); Maeda, et al., Clin. Pathol. 9; 555-558 (1982). Combining direct current and alternating current impedance, special acidic hemolysis in basophile channel and alkali hemolysis in eosinophil channel, a 5-part leukocyte differential can be achieved. Tatsumi, et al., *Sysmex J. Int.* 9; 9-20 (1999).

Alternative optical methods are based on light scattering and fluorescence staining of organelles, granules, and nuclei. Generally, low-angle scattered light contains information on cell size and high-angle scattered light can be used to probe internal composition of the cell. To achieve 5-part differential, certain leukocyte populations, such as eosinophils, require special stain to change its scattering characteristics from other granulocytes, and basophils typically need to be counted separately following the differential lysis of other leukocytes. McKenzie, *Clinical Laboratory Hematology*, Prentice Hall, 2004; Fujimoto, *Sysmex J. Int.* 9 (1999).

In general, conventional automated cell analyzers are bulky, expensive, and mechanically complex, which restricts their locations to hospitals or central laboratories. Conventional cell analyzers require larger sample volumes and generate more waste than the systems developed using microdevices. Furthermore, for analysis of certain cell types, such as leukocytes, accuracy and speed of counting, differentiation, and/or sorting is important for determining disease state and treatment.

SUMMARY OF THE INVENTION

Certain embodiments disclosed herein include a microfluidic apparatus comprising a substrate having a first channel having a defined physical feature, wherein said first channel is in fluid communication with at least one inlet for receiving a fluid, wherein said first channel leads to a restrictive access, and wherein said first channel is in fluid communication with a second channel having a defined physical feature, wherein said second channel is in fluid communication with at least one fluid flow outlet; and a fluid biological sample. In certain embodiments, said defined physical feature is a depression or protrusion. In particular embodiments, said fluid biological sample comprises blood. In certain embodiments, the microfluidic apparatus further comprises a detection zone, and/or a filter array, each in fluid communication with said channel and said fluid flow outlet.

A microfluidic apparatus comprising a substrate having at least one first channel having a defined physical feature; at least one first inlet formed in said first channel for receiving a first fluid; wherein said first channel is in fluid communication with a bifurcated channel, wherein said bifurcated channel is in fluid communication with a third channel detection zone; at least one second inlet for receiving a second fluid, wherein said second inlet is in fluid communication with a branched channel; a filter structure in fluid communication with a reservoir, wherein said reservoir is in fluid communication with said third channel detection zone; at least one fluid flow outlet formed in said third channel; and a fluid sample; wherein the ratio of the cross-sectional area of said second channel compared to the cross-sectional area of said first channel is 1:10. In certain embodiments, the defined physical feature is a depression or a protrusion.

In certain embodiments, said filter structure comprises a filter array, said first fluid comprises sheath fluid and said second fluid comprises blood.

Certain embodiments disclosed herein relate to a detection system comprising microfluidic apparatus and further comprising a light source; a lens assembly; a filter assembly; and an image capture device. In some embodiments, the detection system further comprises at least one display unit or at least one recording unit. In certain particular embodiments, said excitation source comprises a laser, particularly an argon laser. In particular embodiments, said filter assembly comprises an excitation filter, and at least one emission filter. In certain embodiments, said filter assembly further comprises at least one aperture and at least one neutral density filter. In particular embodiments, said filter assembly further comprises at least one glass polarizer.

In certain embodiments, the lens assembly of the detection system comprises at least one condenser lens, at least one objective lens, and at least one beamsplitter. In particular embodiments, said image capture device comprises at least one CCD camera, CMOS device, photodiode, or photomultiplier tube. In certain embodiments, said filter assembly comprises at least two emission filters and said image capture device comprises at least one photomultiplier tube. In certain embodiments, said display unit comprises a computer and said recording unit comprises an oscilloscope. In particular embodiments, said excitation source comprises an argon laser; said lens assembly comprises a condenser lens, an objective lens, and a beamsplitter; said filter assembly comprises an excitation filter, a pinhole aperture and a neutral density filter, and at least one emission filter; said image capture device comprises a CCD camera and a photodiode, and said display unit comprises a personal computer, and further comprising an amplifier.

In particular embodiments, said excitation source of the detection system comprises an argon laser; said lens assembly comprises a condenser lens, an objective lens, and a beamsplitter, said filter assembly comprises an excitation filter, at least one emission filter; said image capture device comprises a photomultiplier tube, and said display unit comprises a personal computer.

Other embodiments disclosed herein relate to a method for identifying a target comprising providing a fluid sample to at least one microfiuldic apparatus, wherein said fluid sample contains at least one dye; providing an excitation source to induce at least one fluorescent signal in a target; detecting the fluorescent signal using as sensor in the apparatus; and identifying the target based in part on the analysis of the fluorescent signal. In certain embodiments, said target is selected from the group consisting of: cells, organelles, nuclei, granules, DNA, and RNA. In other embodiments, said target comprises a cell selected from the group consisting of a monocyte, a granulocyte, a macrophage, a neutrophil, an eosinophil, a basophil, or other leukocyte. In specific embodiments, said target comprises a leukocyte and said dye comprises acridine orange. Particular embodiments of the method further comprising counting or sorting the target in the sample by analysis of the fluorescent signal. In certain embodiments, said fluid sample comprises blood.

DETAILED DESCRIPTION OF THE INVENTION

The present disclosure relates to fabricated microfluidic devices that can be utilized as cell sensors and/or actuators. In certain embodiments, the microfluidic device may be used for labeling, sensing, differentiating, and/or sorting cell populations.

Microfluidic cell sensors and actuators can provide cell sensing and counting for a more accurate outcome and a lower cost. Particle counting (including bead, erythrocyte, and cultured cell) has been demonstrated, for example, by electrical impedance sensing, light scattering detection, and fluorescent sensing. Gawad, et al. *Lab Chip* 1; 76 (2001); Lee, et al. *Proceedings of the 18th IEEE International Conference on Micro Electro Mechanical Systems (MEMS)* 678-681 (2005); Satake et al. *Sens. Actuators B: Chem.* 83; 77 (2002); Morgan, et al. *Curr. Appl. Phys.* 6, 367-370 (2006); Lee et al., *J. Micromech. Microeng.* 15; 447-454 (2005); Altendorf, et al. *Proceedings of the International Conference on Solid State Sensors and Actuators (Transducers '97)* v.1, p. 531, Chicago, Ill. (1997); Holmes et al., *Biosens. Bioelectron.* 21; 1621-1630 (2006); Yang et al., *Meas. Sci. Technol.* 17; 2001-2009 (2006); Simonnet et al., *Anal. Chem.* 78; 5653-5663 (2006); Niehren, et al., *Anal. Chem.* 67; 2666-2671 (1995).

In the area of optical sensing, microfabrication has allowed development of microdevices to replace glass capillary-based flow chambers, and to integrate compact optics and provide on-chip sample transport.

Cell sensing and counting, particularly of leukocytes, is cumbersome due in part to the cell population numbers. For leukocyte differential in microdevices based on optical sensing, a V-groove microchannel was fabricated by anisotropic wet etching of a silicon substrate and 3-part leukocyte differential was demonstrated for diluted blood without sheath flow by two-parameter light scattering. Altendorf, *Proceedings of the Int'l Conference on Solid State Sensors and Actuators*, v. 1, p. 531 (1997).

However, until the instant embodied disclosure, it was necessary to dilute cell samples for cell sensors and actuators for many reasons. One reason dilution has been necessary is in order to prevent the coincidence effect in which multiple cells appear in the detection zone simultaneously. In human blood, the ratio of erythrocytes, or red blood cells, to leukocytes is on the order of about a thousand to one, a dilution factor of from about one hundred to several tens of thousands is typically required to avoid erythrocyte interference for electrical impedance or light scattering detection. Furthermore, for counting leukocytes in samples where leukocytes are specifically fluorescently labeled, a dilution of at least ten times is usually required. Sheenan and Storey, *J. Pathol. Bacteriol.* 59; 336 (1947); Kass, *J. Clin. Pathol.* 76; 810-12 (1981); Weigl et al., *Biomed Microdev.* 3; 267-274 (2001).

Dilution is also often required in order to avoid clogging sample chambers, and also in order to remove erythrocytes that are lysed prior to running the sample, particularly for electrical impedance or light scattering detection. Some of these protocols also require an additional fixation buffer.

Dyes

Figure 1:
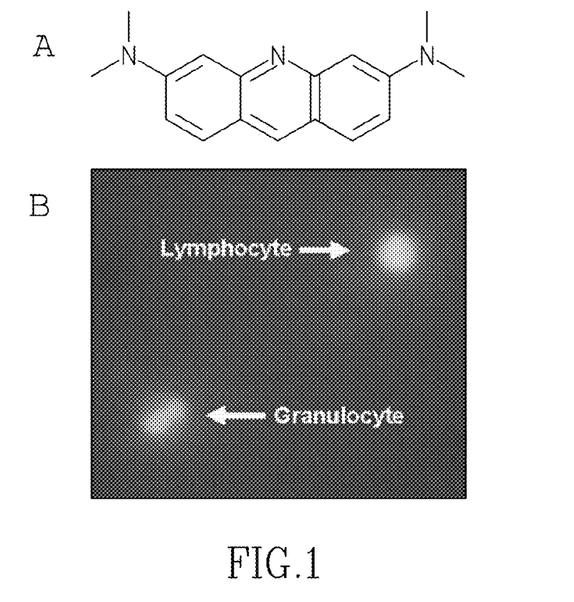
FIG. 1A shows the molecular structure of acridine orange.
FIG. 1B shows leukocyte staining results with acridine orange.

In the present disclosure, a dye, such as Acridine orange (3,6-dimethylamineoacridine, FIG. 1), can be used to differentiate a target, such as cells, organelles, granules, nuclei, molecules (including double or single stranded nucleic acids, such as DNA, or RNA, chromosomes, and also including synthetic forms). In one particular embodiment, leukocytes may be detected, counted, or sorted without need for lysing erythrocytes or fixing the cell sample. Certain dyes, such as Acridine orange, are also desirable due to the fast diffusion into cells, easy commercial availability, and excitation and emission wavelength compatibility with common light sources (i.e. argon laser and other broad spectrum light sources in visible range) and optical filters. Kosenow, *Acta Haematol.* 7, 217 (1952); Schiffer, *Blood*, 19, 200 (1962); Jackson, *Blood*, 17, 643 (1961); Hallermann et al., *Verh Deutsch Ges Inn Med.* 70, 217 (1964).

Acridine orange is a pH-sensitive fluorescent cationic dye that binds to double-stranded DNA by electrostatic attraction and intercalation of the Acridine orange between base pairs. Upon binding, the excitation maximum becomes 502 nm and the emission maximum becomes 525 nm (green). Acridine orange also binds to RNA and single-stranded DNA, with a shifted excitation maximum of 460 nm and an emission maximum of 650 nm (red). Adams and Kamentsky, *Acta Cytol.* 15, 289 (1971); Adams and Kamentsky *Acta Cytol.* 18, 389-91 (1974); Steinkam et al., *Acta Cytol.* 17, 113-17 (1973). Acridine orange is also desirable in that it is hydrophobic in neutral pH, and can easily diffuse through the cell membrane and cell nuclear membrane to bind to RNA and DNA. In living cells, Acridine orange is protonated in the acidic environment of lysosomes, which makes it cationic, and prevents the dye from leaking out of lysosome membranes. Moriyama et al., *J. Biochem.* 92; 1333-36 (1982). When Acridine orange is used for leukocyte analysis, the cell nucleus is stained green with slightly mixed red, a result of double-stranded DNA and single-stranded RNA while the cell cytoplasm is stained red due to the RNA and lysosomes. Thus, leukocyte counting can be achieved easily by using the strong signal from the green fluorescent channel. Leukocyte differentiation can be achieved by analyzing the signal from the red fluorescence channel.

For fresh-stained leukocytes, a 3-part differential (lymphocytes, monocytes, and granulocytes) can be achieved by studying the red fluorescent signal of an Acridine orange stained diluted blood sample, whereas a 5-part differential leukocytes (lymphocytes, monocytes, neutrophils, eosinophils, and basophils) has been demonstrated with hypotonic dilution and fresh Acridine orange-stained leukocyte samples. Adams and Kamentsky, *Acta Cytol.* 15, 289 (1971); Adams and Kamentsky, *Acta Cytol.* 18, 389-391 (1974); Steinkam et al., *Acta Cytol,* 17, 113-17 (1973).

Other dyes can be utilized with certain embodiments described in the instant disclosure, such as ethidium bromide, three-dye combinations (ethidium bromide, brilliant sulflaflavine, and stilbene disulfonic acid derivative); oxazine dyes, basic orange 21, and a polymethine dye. Shapiro, et al., *Histochem. Cytochem.* 24, 396-411 (1976); Shapiro, et al., *J. Histochem. Cytochem.* 25, 836-844 (1977); U.S. Pat. No. 4,376,820; U.S. Pat. No. 4,882,284; Tibbe, et al., *Nat. Biotechnol* 17, 1210-1213 (1999); U.S. Pat. No. 4,400,370; Kass, *J. Histochem. Cytochem,* 36, 711-715 (1988).

Apparatus

One embodiment of the instant disclosure relates to a device or apparatus for cell counting and/or differentiating. In particular embodiments, the device or apparatus comprises a substrate formed from a material, such as silicon, glass, plastic, metal, or other material. One particular embodiment of the instant disclosure was fabricated using soft lithography. Quake, *Science* 290, 1536-40 (2000). Other photolithographic or etching techniques could also be used, according to specific embodiments.

One embodiment of the device was microfabricated using two parts of PDMS (polydimethylsiloxane) (Sylgard 184, Dow Corning, Mich., USA) mixed vigorously in 10:1 ratio. After degassing in vacuum for about 30 minutes, the mixture was poured onto DRIE-etched silicon mold, that had been pretreated with HMDS (hexamethyldisilazane) for easy separation after baking. The molds were baked at 80° C. for 30 minutes. The hardened PDMS was separated from the silicon mold, and PDMS sheet was cut into pieces and fluidic access holes were punctured on each piece with a Luer stub adapter (Becton Dickinson, NJ, USA). Each PDMS piece was carefully placed on a cleaned glass slide and baked overnight at 80° C. In some cases, oxygen plasma treatment (300 m Torr, 25 W, 30 s) was used for PDMS and glass slides in order to improve adhesion between them, particularly with devices that were intended to be reused. Bhattacharya et al., *J. Microelectromechan. Syst.* 14, 590-97 (2005).

In one particular embodiment, the channel structure was molded on a 1 cm×1 cm PDMS block, with the thickness of the PDMS block at less than 3 mm. In one particular embodiment the channel depth was 16 µm in order to accommodate large leukocyte sizes.

Figure 2:
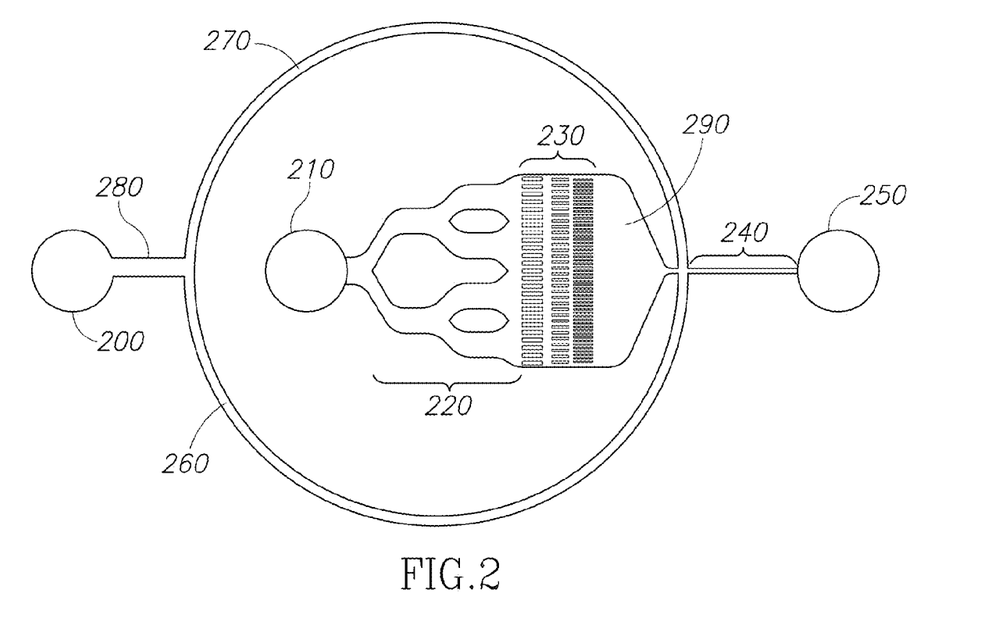
FIG. 2 shows the top view of one embodiment of a novel fabricated microfluidic apparatus.

One exemplary embodiment of the device is shown in FIG. 2. For this particular embodiment, a first fluid flow inlet 200 allows for deposition of, for example sheath flow fluid, and is in fluid communication with a bifurcated channel with a first channel arm 260 and a second channel arm 270 that both converge at a junction of a reservoir 290 and the detection zone 240. In this particular embodiment, the apparatus further comprises a second fluid flow inlet 210 that allows for deposition of, for example, a sample fluid, such as blood, that is in fluid communication with a filter array structure 230, by way of a branched sample flow zone channel 220 and a fluid flow outlet 250. In this particular exemplary embodiment, 2-D hydrodynamic focusing was adopted to control the particle position of the cell sample in the detection zone 240. According to the embodiment shown in FIG. 2, the ratio of cross-sectional area of sheath flow to core sample flow was 10:1, and the channel width of the detection zone 240 was 50 µm, with the width of the focused sample flow preferably 5 µm or less. In particular embodiments, the channels comprise a physical feature, such as a depression or a protrusion.

Figure 13A:
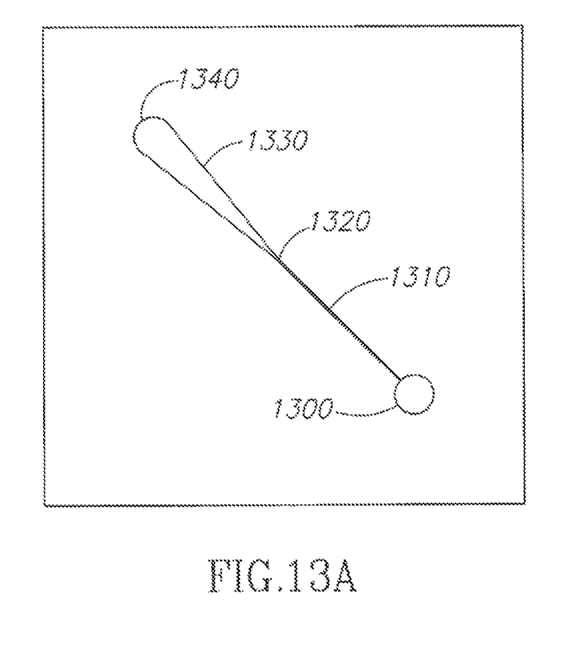
FIG. 13A shows the top view of an apparatus according to one particular embodiment.

One other exemplary embodiment of the device is shown in FIG. 13A. For this particular embodiment, the fluid flow inlet 1340 allows for deposition of a sample fluid, such as a biological sample, or other fluid sample containing a target. In one particular embodiment, the biological sample includes a cell sample, such as blood. In this exemplary embodiment, the fluid inlet is in fluid communication with a first channel 1330 which contains a restrictive access 1320 that is juxtaposed to a second channel 1310 which comprises the detection zone which is also in fluid communication with the fluid flow outlet 1300. In certain embodiments, the height of the first and/or second channels is approximately 5 µm, approximately 8 µm, approximately 10 µm, approximately 12 µm, approximately 15 µm, approximately 20 µm, approximately 25 µm, approximately 30 µm, approximately 35 µm, approximately 40 µm, or any value therebetween. In certain embodiments the width of the second channel is approximately 5 µm, 10 µm, approximately 15 µm, approximately 20 µm, approximately 25 µm, approximately 30 µm, approximately 35 µm, approximately 40 µm, approximately 45 µm, approximately 50 µm, or any value therebetween. In the exemplary embodiment shown in FIG. 13A, the second channel width was approximately 20 µm in size.

Figure 13B:
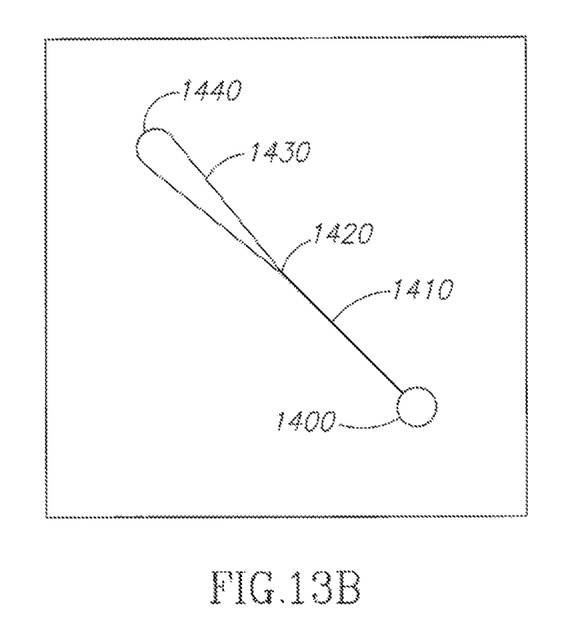
FIG. 13B shows the top view of an apparatus according to one particular embodiment.

One other exemplary embodiment of the device is shown in FIG. 13B. For this particular embodiment, the fluid flow inlet 1440 allows for deposition of a sample fluid, such as a biological sample, or other fluid sample containing a target. In one particular embodiment, the biological sample includes a cell sample, such as blood. In this exemplary embodiment, the fluid inlet is in fluid communication with a first channel 1430 which contains a restrictive access 1420 that is juxtaposed to a second channel 1410 which comprises the detection zone which is also in fluid communication with the fluid flow outlet 1400. In certain embodiments, the height of the first and/or second channels is approximately 5 µm, approximately 8 µm, approximately 10 µm, approximately 12 µm, approximately 15 µm, approximately 20 µm, approximately 25 µm, approximately 30 µm, approximately 35 µm, approximately 40 µm, or any value therebetween. In certain embodiments, the width of the second channel is approximately 5 µm, 10 µm, approximately 15 µm, approximately 20 µm, approximately 25 µm, approximately 30 µm, approximately 35 µm, approximately 40 µm, approximately 45 µm, approximately 50 µm, or any value therebetween. In the exemplary embodiment shown in FIG. 13B, the second channel width was approximately 30 µm in size.

Certain embodiments of the device use a focused laser source for illumination, since cell focusing in the detection zone 240 is highly desirable. However, other embodiments included in the present disclosure use a more uniform diffused light source and a slit aperture. Such embodiments utilize straight channel geometry without cell focusing. In one embodiment, the channel length of the detection zone 240 is 1000 µm. A filter structure 230 upstream of the sample flow zone 220 may also be included in certain embodiments, which filtered out contaminants, including erythryocyte rouleaux, and other large particle aggregates to prevent clogging in the detection zone 240. In certain embodiments, the size of the rectangular pillar structure components of the filter structure 230 was 200 µm×40 µm. The spacing between the pillars in each of the three rows was 40 µm, 30 µm, and 20 µm respectively, which allows for even the largest leukocytes to pass through the filter region 230.

System

Figure 3:
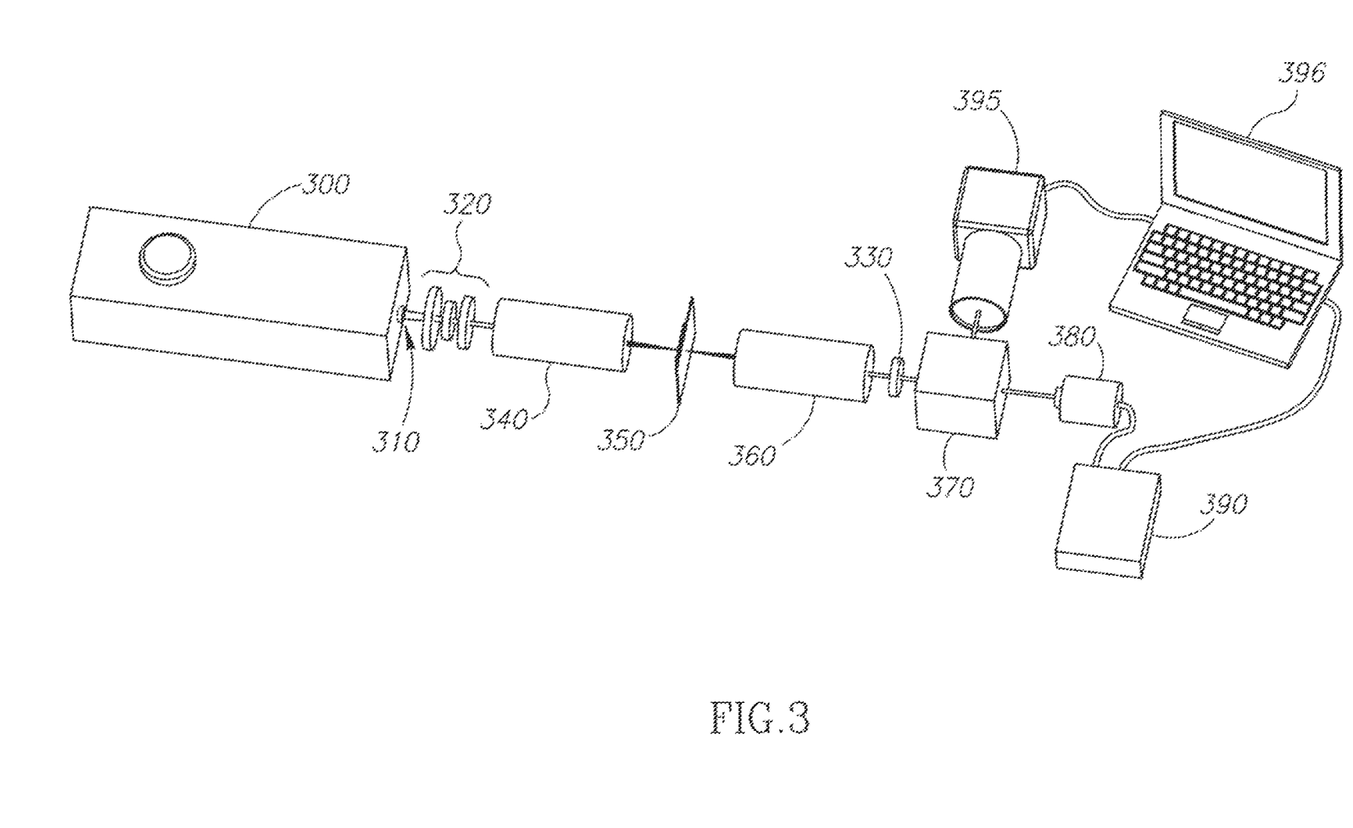
FIG. 3 shows one embodiment of the optical system setup.

The optical system was set up on an optical bench as shown in FIG. 3 (transmitted laser-induced fluorescent detection system or LIF). In one particular embodiment, the system setup comprises an excitation or laser source 300, a lens assembly 340, the microfluidic apparatus 350, an optional additional lens assembly 360, a filter assembly 320, 330, and an image capture device 390, 305. In certain embodiments, one or more emission filters comprise the filter assemblies 320, 330. In certain embodiments, the image capture device 395 comprises a charge coupled device (CCD) camera, a complementary metal-oxide-semiconductor (CMOS) device, or a photomultiplier tube (PMT) device. In particular embodiments, the image capture device 395 may be coupled to communicate with a display unit or computing device 396, such as a personal computer. One of skill in the art would recognize that multiple and various computer software programs are available that allow for integration, compilation, analysis, reconfiguration, and other manipulation of data received from the system, particularly by way of the computing device 396.

In one particular exemplary embodiment, an argon laser (National Laser NLC210BL, 488 nm, and 15-30 mW adjustable, Salt Lake City, Utah, USA) is used as the excitation source. An aperture 310 of 50 µm diameter is put in front of the laser output to facilitate, the alignment process and lower the illumination intensity. In certain embodiments, an optional laser-line bandpass filter (bandwith equal to about 1.9 nm with a central wavelength of 488 nm) is used to further purify the laser source. In certain other embodiments, an optional neutral density filter (NDF) is used to attenuate laser excitation. Alternatively, the pinhole and NDF are replaced by two linear glass polarizers (Edmond Optics TECH SPEC, Barrington, N.J., USA) so that the illumination level on the device can be easily adjusted.

In one particular embodiment, a long-working-distance microscope objective (USMCO M Plan Apo, 10×, 0.28 NA, Dayton, Nev., USA) is used as a condenser lens 340. Another long-working-distance microscope objective (Bausch & Lomb, 50×, 0.45 NA, Rochester, N.Y., USA) is used as an objective lens 380. In the same embodiment, three emission filters 320 are used in one particular test: 488 nm long pass filter (Chroma H1500 LP, transition width<4.9 nm, edge steepness=2.5 nm, Rockingham, Vt., USA), a green bandpass filter with central wavelength 525 nm and a bandwidth 50 nm (Chrome D525__50 m), and a red bandpass filter with central wavelength 650 nm and bandwidth 50 nm (Chrome D650__50 m). A broadband non-polarizing hybrid cube beamsplitter 370 (Newport 05BC17MB.1, 400-700 nm, R/T=45%/45%, Irvine, Calif., USA) is used to direct light to the photodiode detector 380 and CCD camera simultaneously.

The signal is electrically amplified and detected either with a silicon photodiode receiver module 390 (Electro-Optical Systems, UVS-025-H, Phoenixville, Pa., USA) or a photon multiplier tube (PMT, Hamamatsu H5784-20, Japan). The voltage signal is sent to a deep memory oscilloscope (HP 54645A, Palo Alto, Calif., USA). When the buffer in the oscilloscope is full, the data can be loaded to a computer and analyzed with a Matlab peak-detection program. Video may be taken with an analog CCD camera (Hitachi KP-D20B, Japan) at 30 frames per second and then converted to digital format and stored in a computer 396. Other imaging capture devices 395, such as CMOS, PMT, or still other devices may also be used with particular embodiments described herein. In certain exemplary test runs, the system set up utilizing a photodiode detector and PMT are more sensitive than the CCD camera and have a faster time response. During one exemplary test run, the optical system was first roughly aligned on a dummy device with the aid of images from CCD camera. A 10 µm diameter illumination spot on the detection zone is easily achieved with proper alignment.

Figure 12A:
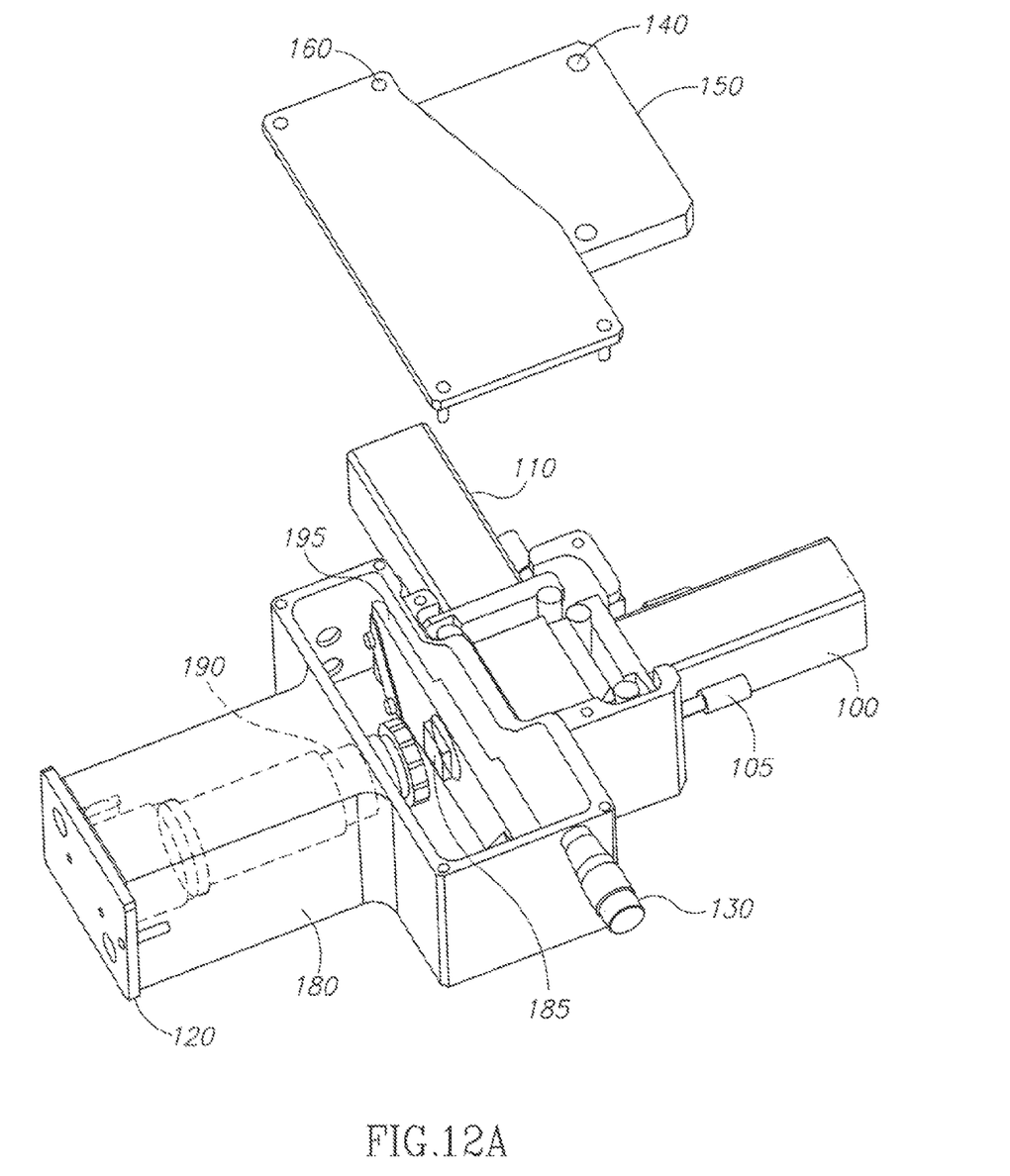
FIG. 12A shows an illustration of a handheld detection box instrument according to one embodiment.
Figure 12B:
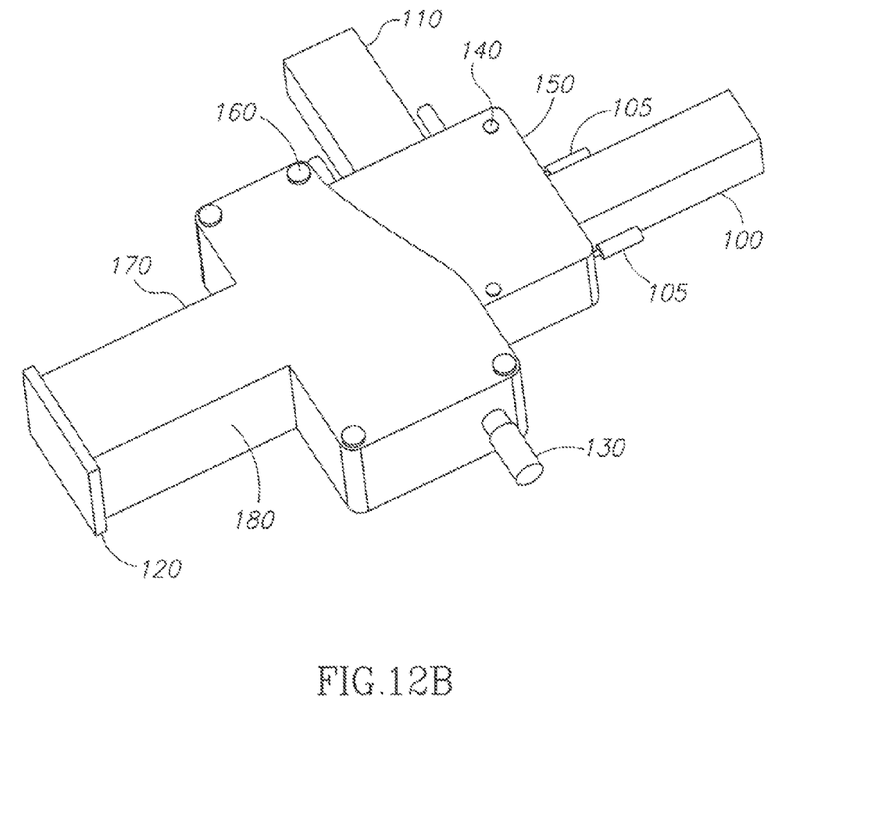
FIG. 12B shows an assembled detection box instrument according to one embodiment.

As shown in FIG. 12A and FIG. 12B, the instant apparatus may be incorporated into a hand-held unit comprising a laser source such as a laser emitting diode or LED 120), at least one lens 190, at least one filter assembly with optional beamsplitter 195, a microfluidic apparatus as described herein on a microchip or other substrate 185, an input/output port 130, at least one image capture device 100, 110, which may be a photomultiplier tube. In certain embodiments, the hand-held unit may be assembled and enclosed by an outer casing or casings 150, 180, and rivets or bolts 140, 160.

Cell Detection

One aspect of the instant disclosure relates to methods of counting and/or differentiating cells, particularly leukocytes, from undiluted cell samples, such as human or other animal blood, by utilizing microfabricated devices. In one exemplary embodiment, cell detection was conducted utilizing Acridine orange and fresh whole human blood.

In one exemplary embodiment, fresh human blood was obtained from healthy donors and used within 3 days of collection. EDTA was added to the blood samples in order to prevent coagulation. For Acridine orange staining, the stock solution was added to obtain a final dye concentration of 10 µg/mL in Ficoll-Paque Plus. Ficoll-Paque Plus was also used as the sheath flow solution. Fluorescent polystyrene beads (5 µm green fluorescent beads) were purchased from Duke Scientific Corporations, Fremont, Calif., USA. Cell nucleus stain Acridine orange was obtained from Molecular Probes, Eugene, Oreg., USA, and dissolved in water to achieve a 10 mg/mL stock solution. Blood diluent Ficoll-Paque Plus was purchased from Amersham Biosciences, Sweden. Phosphate buffered saline (10×PBS) was obtained from Ambion (9625), Austin, Tex., USA.

Staining results were observed under a fluorescent microscope (Nikon E800, Japan) with a triple and filter block DAPI-FITC-TRITC, which has excitation filter wavelengths of 385-400 nm, 475-490 nm, and 545-565 nm, and emission filter wavelengths of 450-465 nm, 505-535 nm and 580-620 nm. Images were taken with a cooled CCD camera (RT-KE color 3-shot, Diagnostic Instruments, Sterling Heights, Mich., USA). Rough count of leukocytes was made with a hemactyometer (Hausser Scientific, Horsham, Pa., USA). When necessary, blood or fluorescent beads were diluted with Ficoll-Paque Plus (specific gravity 1.077 g/mL) to match the specific gravity of the solvent to leukocytes. All fluids were pumped into the devices using syringe pumps (Harvard Apparatus Pico Plus, Holliston, Mass., USA).

In this particular embodiment, an analog CCD camera was used for video recording at a matched camera frame rate of 3 nL/min sample flow rate and 30 nL/min sheath flow rate. For photodiode detection, a 0.1 µL/minute sample flow rate and a 1 µL/minute sheath flow rate were used. A 1 µL/minute sample flow and a 10 µL/minute sheath flow were used with the photon multiplier tube instrument.

Figure 4A:
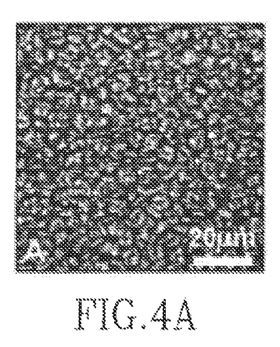
FIG. 4A shows erythrocyte concentration in whole blood.
Figure 4B:
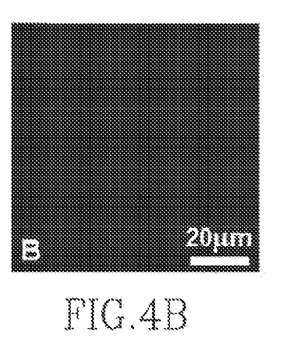
FIG. 4B shows leukocyte staining in whole blood with acridine orange at a concentration of 100 ng/mL.
Figure 4C:
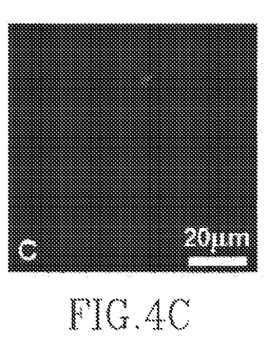
FIG. 4C shows leukocyte staining in whole blood with acridine orange at a concentration of 1 μg/mL.
Figure 4D:
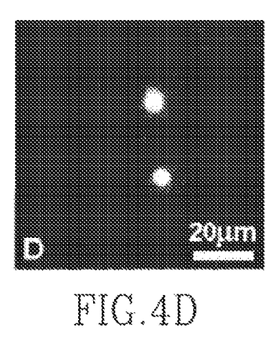
FIG. 4D shows leukocyte staining in whole blood with acridine orange at a concentration of 10 μg/mL.
Figure 4E:
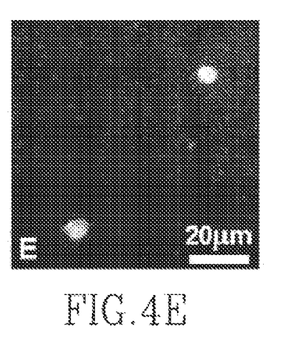
FIG. 4E shows leukocyte staining in whole blood with acridine orange at a concentration of 100 μg/mL.
Figure 4F:
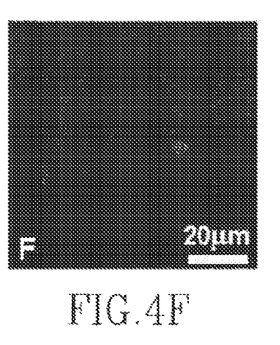
FIG. 4F shows leukocyte staining in whole blood with acridine orange at a concentration of 1 mg/mL.

In order to achieve a high signal-to-noise ratio, the maximal concentration for cell staining was established using routine methods in the art. Adams and Kamentsky, *Acta Cytol.* 15; 289 (1971). As shown in FIG. 4, whole blood samples were analyzed with different Acridine orange concentrations. The optimal concentration for leukocyte staining as determined to be approximately in the range of 1 µg/mL. In the particular exemplary embodiment utilized in FIG. 4, the distance between the coverslip and the grid surface was approximately 100 µm. As can be seen in FIG. 4A, an abundance of erythrocytes were present under the field of view, yet these cells did not interfere with the fluorescent signal from the leukocytes, as shown in FIG. 4B-F.

Figure 5:
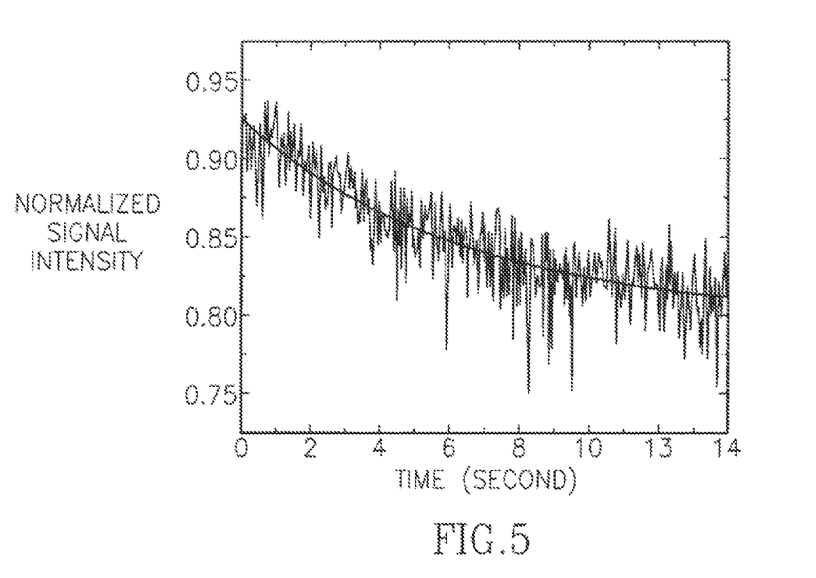
FIG. 5 shows fluorescent signal bleaching from a single leukocyte in one embodiment.
Figure 6A:
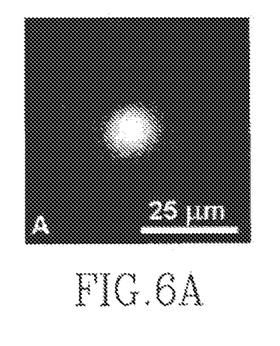
FIG. 6A shows an image of background and a 5 μm bead with focused laser illumination flow taken by CCD camera with long pass emission filter, according to one embodiment.
Figure 6B:
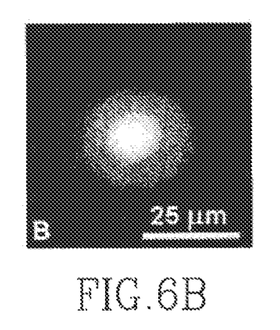
FIG. 6B shows an image of background and a 5 μm bead with laser illumination flow taken by CCD camera with long pass emission filter, according to one embodiment.
Figure 6C:
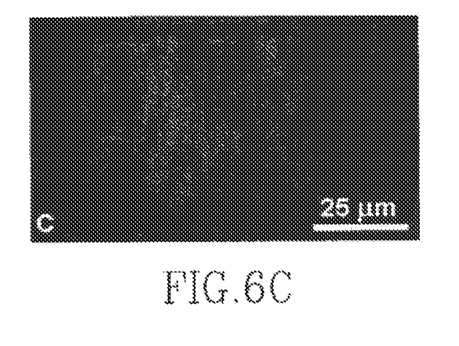
FIG. 6C shows an image of background and a 5 μm bead with diffused laser illumination flow taken by CCD camera with long pass emission filter, according to one embodiment.
Figure 6D:
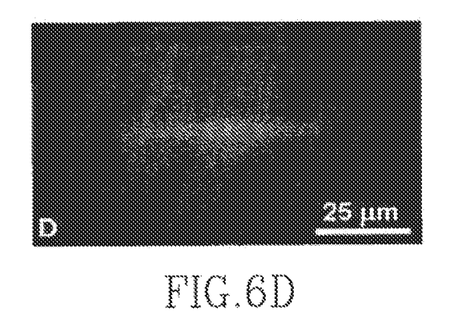
FIG. 6D shows an image of background and the trace of a 5 μm bead with diffused laser illumination flow taken by CCD camera with long pass emission filter, according to one embodiment.

As can be seen in FIG. 5, the exemplary embodiment utilized in cell detection did not experience any significant photobleaching. The signal was fitted as a first-order exponential decay with time constant of 6.4±0.7 seconds. Two more tests confirmed that the photobleaching time constant for one particular embodiment was between 1 second and 10 seconds. The photobleaching time constant for one particular embodiment was characterized by filling the device with Acridine orange-stained whole blood. The channel was scanned by the laser spot and the illumination was set to be the same as that used in testing. The entire process was recorded with a CCD camera. Whenever a fluorescing leukocyte was observed with fluorescent emission clearly distinct from the background, we stopped moving the laser spot and waited until the leukocyte was photobleached to background level. The images were extracted from the video, converted to 8-bit gray scale images, and analyzed with a Matlab program. The data was fitted to a single time-constant exponential decay.

Figure 7:
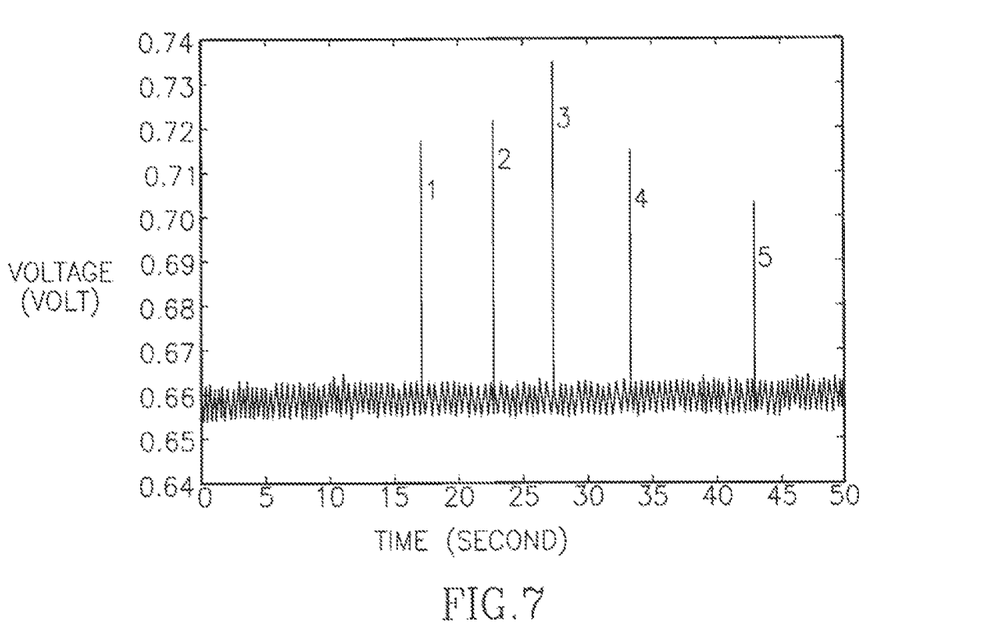
FIG. 7 shows a graph of detection of 5 μm fluorescent beads detection with photodiode detector with long pass emission filter.

Additionally, green fluorescent beads were tested at a concentration of about $2\times10^3/\mu L$, as observed by CCD camera, and shown in FIG. 6. Sample flow rate was set at about 3 nL/min, and sheath flow was about 30 nL/min. In one exemplary test run, a hydrodynamic focused laser beam, as shown in FIG. 6A, created an enlarged light circle as shown in FIG. 6B. Only a single bead normally appeared in each image. With diffused laser illumination, as shown in FIG. 6C, the trace of the bead could be identified, as shown in FIG. 6D. Hydrodynamic focusing limits the cross-sectional area of the detection zone without shrinking the channel diameter, thus the signal-to-noise ratio may be improved without increasing the risk of clogging the channel. Also, the reduction of the cross-section of the core flow reduces the coincidence effect. Finally, enclosing the core sample flow with sheath flow minimizes fluorescent dye absorption in the device walls, thus reducing background noise. As indicated in FIG. 7, bead signals from the photodiode detector could easily be identified.

Figure 8A:
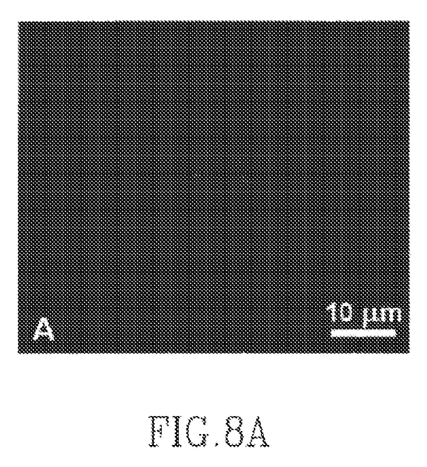
FIG. 8A shows background image of focused laser beam from video taken by CCD camera with long pass emission filter, according to one embodiment.
Figure 8B:
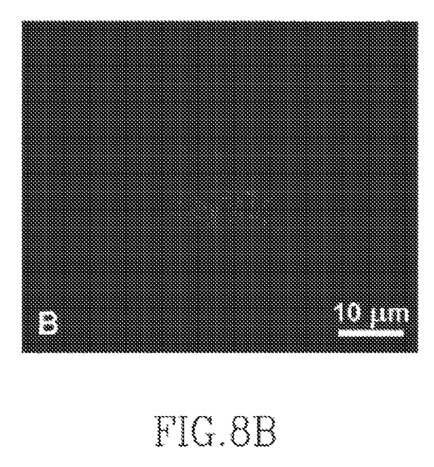
FIG. 8B shows a signal from a leukocyte from diluted whole blood testing from video taken by CCD camera with long pass emission filter, according to one embodiment.

As shown in FIG. 8, using both red and green emission filters, images extracted from video taken by the CCD camera show the signal identified from a leukocyte stained with Acridine orange, as well as the signal obtained from the fluorescent control bead. For photodiode detection, the expected leukocyte detection rate would average about 4-11 cells per second for a normal individual.

Figure 9:
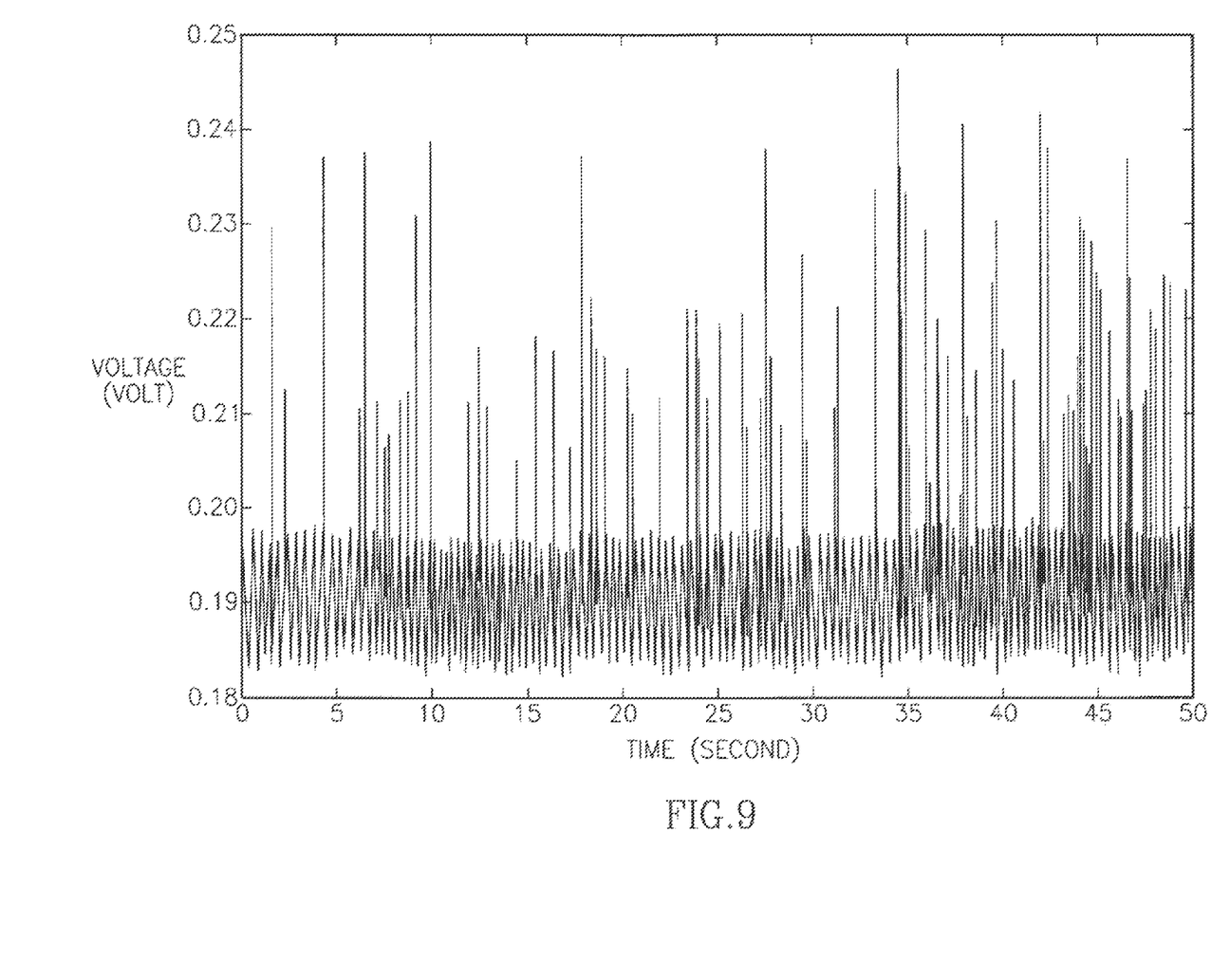
FIG. 9 shows the time trace of amplified photodiode signal of acridine orange stained undiluted whole blood with green emission filter centered at 525 nm, and peaks labeled, according to one embodiment.
Figure 10:
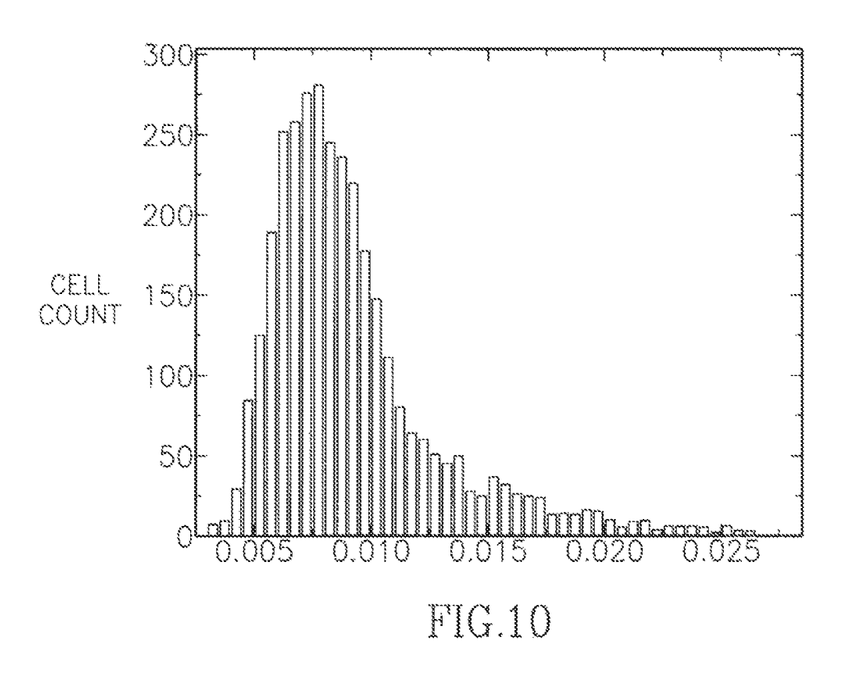
FIG. 10 shows a histogram of signal intensity from photodiode detector with green emission filter centered at 525 nm.

In one exemplary embodiment, a time trace over 50 seconds of an undiluted blood sample stained with Acridine orange using a green emission filter, and a throughput of up to about 1000 leukocytes per second was attained. Maxima signal intensity (peak height as in FIG. 9) from the green fluorescent channel with 525 nm emission filter was studied by plotting its histogram, as shown in FIG. 10. As expected, the lower-intensity portion is likely contributed mainly by lymphocytes, while the higher-intensity portion is likely mainly from monocytes, with the center-region is likely mostly from granulocytes, Steinkam et al., *Acta Cytol*, 17; 113-117 (1973).

Figure 11:
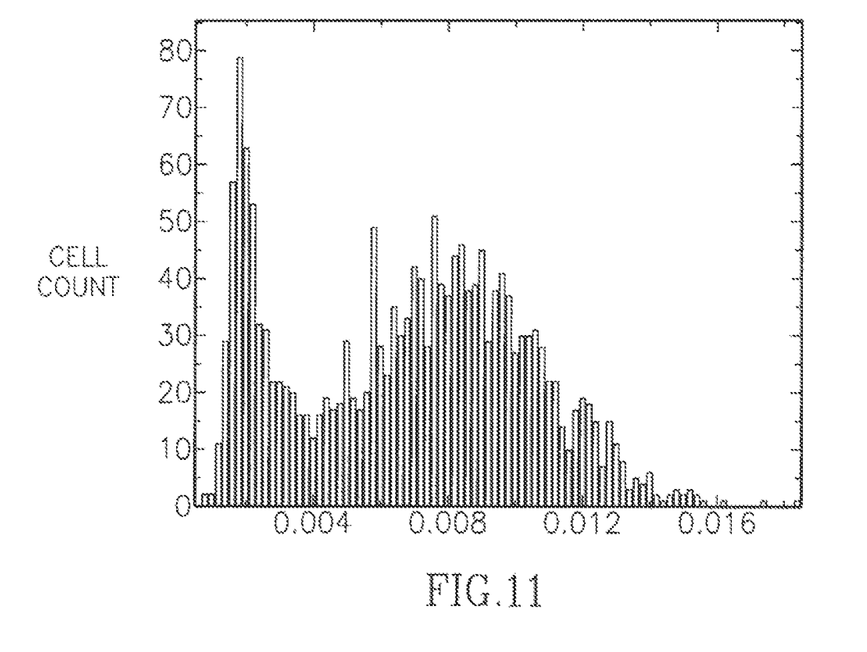
FIG. 11 shows a histogram of signal intensity from photodiode detector with red emission filter centered at 650 nm.

In one exemplary embodiment, a time trace over 50 seconds of an undiluted blood sample stained with Acridine orange using a red fluorescent channel with 650 nm emission filter was conducted. As shown in FIG. 11, two peaks were identified, the lower intensity is dominated by lymphocytes and the higher-intensity peak is largely monocytes and granulocytes. The time between the start of staining the cells to photodiode recording was typically greater than 15 minutes.

In both exemplary studies, the maximal throughput was about 1000 leukocytes per second utilizing one embodiment of the PMT detector. By using undiluted blood, minimal sample volume was maintained, which increases the throughput. Since sample throughput is proportional to volume flow rate, but is limited by the maximal pumping rate and response time of the sensing system a 3 nL/minute core flow rate was used with the CCD camera detection. Under this flow rate, a typical leukocyte traveled through the detection zone in approximately 30 milliseconds, which roughly equals the CCD frame acquisition time.

How rates for varying embodiments may be suitable for a range from approximately 1 nL/minute, approximately 2 nL/minute, approximately 3 nL/minute, approximately 4 nL/minute, approximately 5 nL/minute, approximately 6 nL/minute, approximately 7 nL/minute, approximately 8 nL/minute, approximately 9 nL/minute, approximately 10 nL/minute, approximately 20 nL/minute, approximately 30 nL/minute, approximately 40 nL/minute, approximately 50 nL/minute, approximately 60 nL/minute, approximately 70 nL/minute, approximately 80 nL/minute, approximately 90 nL/minute, approximately 100 nL/minute, approximately 110 nL/minute, approximately 120 nL/minute, approximately 130 nL/minute, approximately 140 nL/minute, approximately 150 nL/minute, or any value therebetween for photodiode detection. Likewise, for PMT detection, flow rates for varying embodiments may be suitable for a range from approximately 200 nL/minute, approximately 300 nL/minute, approximately 400 nL/minute, approximately 500 nL/minute, approximately 800 nL/minute, approximately 700 nL/minute, approximately 800 nL/minute, approximately 900 nL/minute, approximately 1 µL/minute, approximately 2 µL/minute, approximately 3 µL/minute, approximately 4 µL/minute, approximately 5 µL/minute, or any value therebetween.

In one exemplary embodiment, the time response of the photodiode receiver module under low sensitivity setting was 0.16 milliseconds, and 0.6 milliseconds under high sensitivity, while the time response of the PMT detector in one exemplary run was about 16 microseconds.

Furthermore, by decreasing the cross-sectional area, the linear flow velocity of the core flow is increased, which requires faster sensing, and reduces the coincidence effect by increasing the average distance between cells in the detection zone.

Thus, by utilizing particular embodiments disclosed herein relating to a microfluidic device, leukocyte sensing, counting, and sorting can be achieved one-by-one in a micro flow cytometer system. Furthermore, dense cell suspensions, such as whole, undiluted blood may be utilized in certain embodiments described herein, which provides for reduced sample and waste volume, reduced processing time, and completely eliminates on-chip mixing and buffer storage. In particular aspects, leukocytes can be sensed one-by-one in a micro flow cytometer system.

As described herein, certain embodiments of the device can be implemented in various sizes and conformations, including but not limited to a bench-top device, a handheld device (such as is shown in FIG. 12), an implantable device, a nanotechnology device, or other size or conformation. In the smaller exemplary conformations, high-illumination LED is used for excitation and a minipump is used to manipulate the sample in suction mode, while fluorescent signals from green and red channels can be detected simultaneously.

INCORPORATION BY REFERENCE

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The invention claimed is:

1. A method for analyzing leukocytes in a whole blood sample, the method comprising:
    a) introducing a modified blood sample comprising fluorescently labelled leukocytes and fluorescently labeled control beads, to an inlet of a first microfluidic channel that gradually narrows and is directly coupled to a second microfluidic channel that has fixed dimensions, wherein the fluorescently labeled leukocytes are labelled with a fluorophore different than a fluorophore label of the control beads, and wherein the second channel having the fixed dimensions of approximately 40 microns by approximately 50 microns, and wherein the first channel and the second channel are obstacle-free;
    b) flowing the modified blood sample from the inlet of the first microfluidic channel, to the outlet of the second microfluidic channel, whereby decreasing the cross-sectional area increases a core flow rate of the modified blood sample, such that the core flow rate is from approximately 5 microliters/minute at a detection zone located in the second microfluidic channel;
    c) detecting a level of fluorescence of the fluorescently labelled leukocytes and a level of fluorescence of the fluorescently labelled control beads, as they pass through the detection zone in the second microfluidic channel, by exciting the fluorophores of the fluorescently labelled leukocytes and of the fluorescently labeled control beads, wherein the detection of the leukocytes is performed on individual leukocytes; and
    d) using the level of fluorescence to thereby provide a result concerning the blood sample.

2. The method of claim 1, wherein the method further comprises identifying the fluorescently labelled leukocytes.

3. The method of claim 1, wherein the method further comprises sorting the fluorescently labelled leukocytes.

4. The method of claim 1, wherein the method further comprises counting the fluorescently labelled leukocytes.

5. The method of claim 1, further comprising recording measurement on a recording unit.

6. The method of claim 1, further comprising recording the result on a recording unit.

7. The method of claim 1, wherein the method can detect leukocytes at a rate of up to about 1000 leukocytes per second.

8. The method of claim 1, further comprising using an excitation source to excite the fluorophores of the fluorescently labelled leukocytes and of the fluorescently labeled control beads.

9. The method of claim 8, wherein the excitation source is a laser or a LED.

10. The method of claim 1, wherein the excitation source further comprises a lens assembly.

11. The method of claim 1, further comprising measuring the fluorescence of the fluorescently labeled leukocytes and of the fluorescently labeled beads using a light sensor.

12. The method of claim 11, wherein the light sensor comprises a photomultiplier.

13. The method of claim 1, further comprising manipulating the fluorescence measurement using a computer software inscribed on a computing device.

14. The method of claim 13, further comprising displaying a result of the manipulation on a display unit.

15. The method of claim 1, wherein the fluorescently labeled beads are polymeric beads.

16. The method of claim 1, wherein the fluorescently labeled beads are polystyrene beads.

17. The method of claim 1, wherein the measurement of the fluorescence comprises using an image capture device.

18. The method of claim 1, wherein the flow of the modified blood sample is performed by pumping the fluid sample through the microfluidic device.

19. The method of claim 1, wherein the modified blood does not comprise a sheath fluid.

* * * * *